United States Patent [19]
Toth

[11] 3,936,163
[45] Feb. 3, 1976

[54] VISION EXAMINATION LENS SYSTEM

[75] Inventor: John E. Toth, San Diego, Calif.

[73] Assignee: Gilber B. Razran, San Diego, Calif.

[22] Filed: Sept. 10, 1973

[21] Appl. No.: 395,658

[52] U.S. Cl. .............................. 351/17; 350/191
[51] Int. Cl.² .................. A61B 3/02; G02B/3/06
[58] Field of Search .............. 351/17, 27, 34, 6, 36; 350/189, 190

[56] References Cited
UNITED STATES PATENTS

| | | | |
|---|---|---|---|
| 667,973 | 2/1901 | Cross | 351/27 |
| 698,833 | 4/1902 | Hardy | 351/17 |
| 2,087,235 | 7/1937 | Ames, Jr. et al. | 351/27 X |
| 3,507,565 | 4/1970 | Alvarez et al. | 350/189 |

*Primary Examiner*—Paul A. Sacher
*Attorney, Agent, or Firm*—Brown & Martin

[57] ABSTRACT

An optical system utilizing a single spherical and two cylindrical lenses. The cylindrical lenses are located along the optical axis of the spherical lens and between the spherical lens aand an optical target. A first of the cylindrical lenses is fixed longitudinally but rotatable. The second cylindrical lens rotates with the first, but is relatively translatable along the optical axis. When the cylindrical lenses are nearly in contact, their net power is zero, and the patient views the target with the effect of the spherical lens' power only. The requisite spherical correction is determined by moving the target along a track that extends from a location well within the focal length of the spherical lens to a location well beyond it. Cylindrical correction is obtained by a combination of rotation and extension of the second cylindrical lens to produce variable negative cylindrical power and axis orientation.

6 Claims, 4 Drawing Figures

VISION EXAMINATION LENS SYSTEM

BACKGROUND OF THE INVENTION

The determination of the proper refractive corrections to obtain maximized vision is normally accomplished utilizing a graded series of lenses which are held in the viewer's line of vision. The patient is asked to relate whether each successive lens produces an improvement or deterioration of the image of a target. Cylindrical correction is similarly obtained by the process of manually rotating the axis of the cylindrical correction through increments until 180° of possible orientation have been experimented with. Proper cylindrical power is then obtained by applying a graded series of cylindrical powers to obtain maximum visual acuity. The determination of the relative power for spherical and cylindrical corrections is always a difficult judgement decision. This and the other judgement decisions associated with a vision examination are compounded when the patient is too young or otherwise unable to adequately express the difference between successive lenses. In view of the many judgement decisions involved throughout the process, it is not possible to delegate the task of refraction to non-professional personnel, and therefore the task is normally carried out by the optometrist or ophthalmologist himself. This results in a relatively inefficient vision examination process and increases the cost of the process.

The deficiencies in the prior art technique for vision examinations have resulted in the development of a number of proposed vision examination aids. Apparatus that detect the angulation of a laser beam, or similar light beam, passed into the eye and reflected from the retina have been developed and marketed. These and other idirect methods have the disadvantage that they are limited to the optical characteristics of the mechanical eyeball itself and do not take into effect the optic nerve and brain functions which produce the total vision system of an individual. Further, the possible eye damage due to excessive power levels in the laser beam and overall complexity of these units has limited the scope of their application.

Therefore it is desirable to have a vision examination apparatus and lens system that facilitates the examination of the human eye from the standpoint of prescribing refractive lenses to the point where portions of the examination can be conducted by non-professional personnel, and wherein the examination includes the total vision system including the brain and optic nerve.

SUMMARY OF THE INVENTION

An exemplary embodiment of the invention is directed to an optical system for testing human vision as in the prescription of corrective lenses. The patient is subjected to an image which varies continuously over a wide range of spherical and cylindrical power corrections, together with the entire arc of axis orientations. A complicated lens system is not required and therefore there is reduction in expense and likelihood of failure, together with potential interference produced by extraneous optical effects from complicated and multiple refractions through a multiple lens system. The spherical correction is obtained by the movement of an illuminated target along the optical axis of the single convex fixed lens. The range of translation of the target is such that the usual spectrum of diopter variations may be obtained in a single translation from a point well within the focal length for the fixed convex lens to a point well beyond that focal length. For the eye with normal or the so called "perfect" vision, the target will appear clearest at the focal length and therefore the reading for this focal length would produce an indication of zero diopter necessary correction. When the target appears clearest at positions beyond the focal length, a positive power lens for correction of a far-sightedness condition is indicated. Alternatively for positions of the target inboard of the focal point, negative power for the correction of a nearsighted condition is indicated.

The mechanisms translating the target between the positions produce greater motion per unit time in the direction of the extreme positive target travel to produce a nearly linear with time diopter variation.

Cylindrical corrections, including axis and negative power, are obtained through the use of paired concave and convex lenses with cylindrical power. The lenses in the plano or spherical correction testing position are spaced by a small air gap. To obtain the zero net power for the lens combination the second or convex cylindrical lens has a slightly greater power than the first or concave lens so that the net effect of the pair at the closest approach is zero. For all other positions with the range of translation for the cylindrical lens, a net negative power along the cylindrical axis is realized. Thus, by a continuous rotation of the cylindrical lens pair and by relative translation of the cylindrical lenses, the patient's vision is subjected to a complete range of cylindrical powers and axis variations. The axis and negative power at which the visual acuity is the greatest is detectable from the physical relationship of the cylindrical lens pair. Therefore, the proper cylindrical correction for the prescriptive lenses may be determined. Mechanical drive features for the cylindrical lens pair in rotation and relative translation are provided to produce minimal objectionable fluctuation in the translation or rotation rate, producing a smooth change in focus and axis of correction and a correspondingly regular sensation to the patient.

The principles of the invention have particular application to vision testing systems utilizing brain wave interpretation. In such systems, electrodes placed in contact with appropriate portions of the user's scalp detect the electrical signals from the responsive section of the patient's brain. By proper interpretation, these signals can determine the point at which the patient's visual acuity is at a maximum. For example, it has been determined that the point at which the brain wave phase shift reaches a maximum corresponds to the point at which the patient's visual acuity reaches a maximum, and therefore, apparatus which is capable of detecting this phase shift is useful in conjunction with the instant invention to produce an indication of maximum visual acuity with the corresponding read-out of the spherical correction and cylindrical correction orientation to produce this visual acuity.

It is therefore an object of the invention to provide a new and improved vision examination lens system.

It is another object of the invention to provide a new and improved vision examination lens system utilizing a relatively simple lens train to obtain a scan of the complete refractive correction spectrum.

It is another object of the invention to provide a new and improved vision examination lens system which is relatively low in cost.

It is another object of the invention to provide a new and improved vision examination lens system which produces a smooth variation in spherical cylindrical power and axis rotation.

It is another object of the invention to provide a new and improved vision examination lens system which is compatible with automatic vision testing apparatus.

It is another object of the invention to provide a new and improved vision examination lens system that incorporates cylindrical correction lenses which have a nominal or zero net correction position.

It is another object of the invention to provide a new and improved vision examination lens system that utilizes a single fixed spherical lens.

It is another object of the invention to provide a new and improved vision examination lens system that does not necessitate the exposing of the eye to concentrated radiation.

Other objects and many attendant advantages of the invention will become more apparent upon a reading of the following detailed description, together with the drawings in which like reference numerals refer to like parts throughout and in which.

Figure 1:
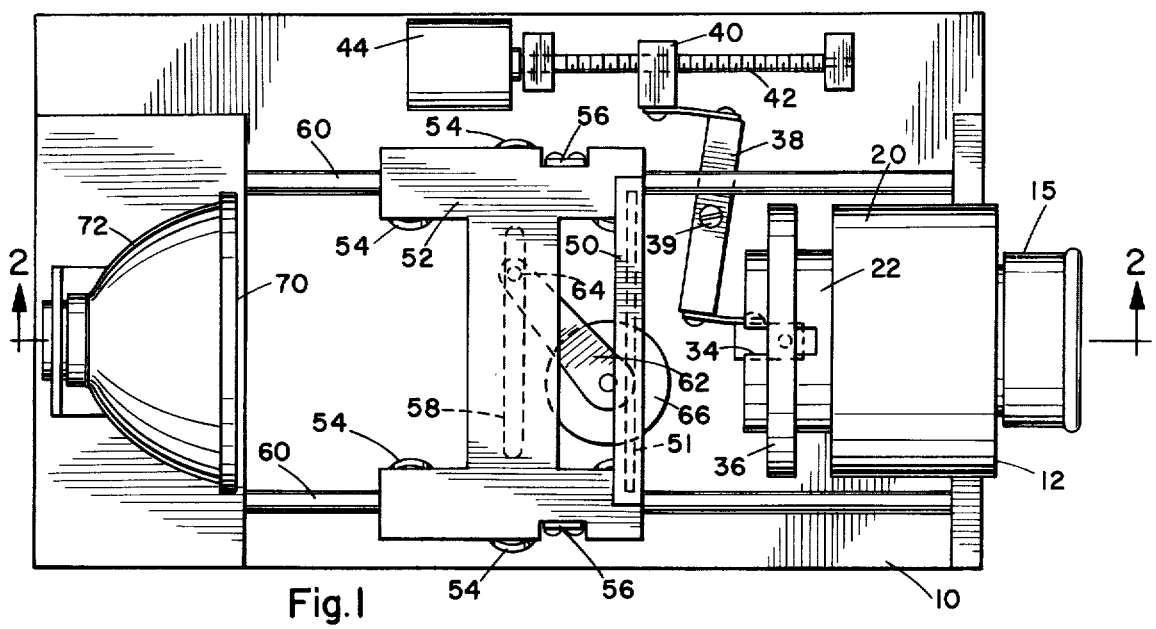
FIG. 1 is a top plan view of the complete apparatus.
Figure 2:
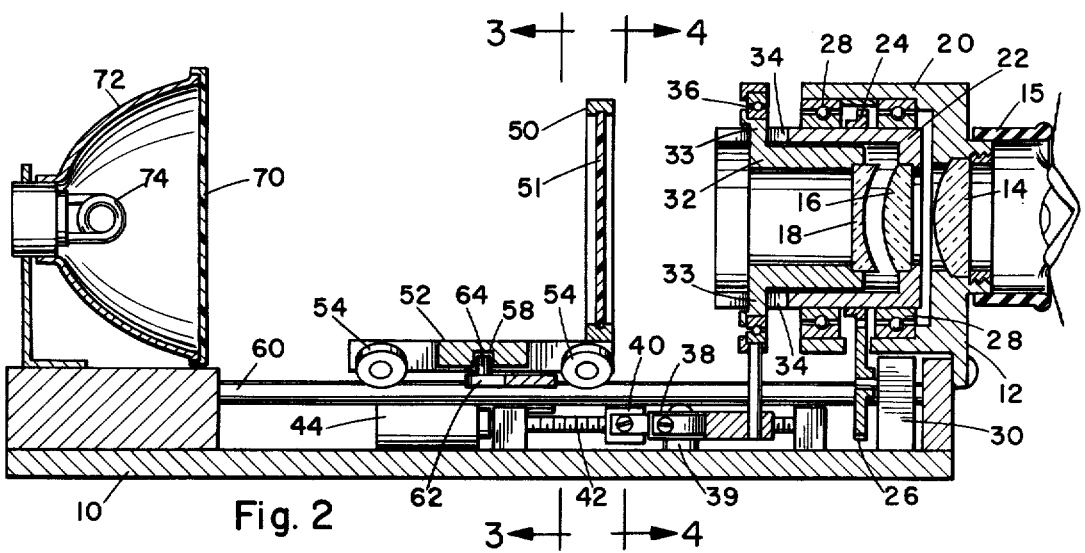
FIG. 2 is a sectional view taken on line 2—2 of FIG. 1.
Figures 3, 4:
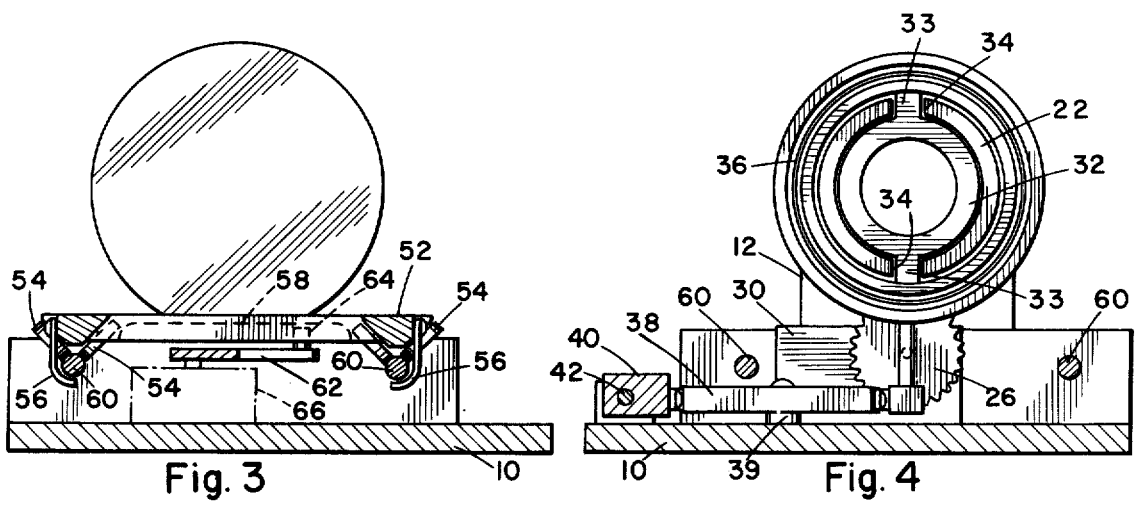
FIG. 3 is a sectional view taken on line 3—3 of FIG. 2.
FIG. 4 is a sectional view taken on line 4—4 of FIG. 2.

Referring now to the drawing, there is illustrated a frame 10. The frame mounts a lens carrier 12 which fixably supports a plano-convex lens 14 having sufficient spherical power to have a focal length falling within the confines of the frame 10. A plano-convex cylindrical lens 16 and a concaveplane cylindrical lens 18 are mounted in the carrier 22 for rotation in barrel portion 20 of carrier 12 on bearings 28. Ring gear 24 on carrier 22 is driven by drive gear 26 which is rotated by a motor 30. The lens 18 is keyed for rotation with carrier 22 by translation carrier 32 which has radial extensions 33 received through slots 34 in the carrier 22. The translation drive mechanism comprises a flexure pivot 38 which is pivoted on a bearing 39 and driven by a nut 40 on shaft 42 of motor 44. The flexure pivot is secured to bearing 36 which permits the translation carrier 32 to rotate with the carrier 22. The target 50 includes a translucent target screen 51 with a checker board pattern. Target 50 is mounted on a carriage 52 and guided on rails 60 by angularly displaced wheels 54. The security of the carriage on the rail is insured by clips 56. Carriage 52 is driven along the rails by a motor 66 which induces carriage movement through an arm 62. The arm 62 has pivot 64 received in transverse slot 58 on the underside of the carriage cross bar 68.

A strobe flash tube 74 is mounted within a reflector housing 72. The housing 72 directs light from the flash tube 74 through a diffuser 70 and on to the rear face of the transparent target screen 51.

OPERATION

In use, a patient places his eye in the proximity of the eye piece 15 and views the target screen 51 through the spherical correction lens 14. The focal length of lens 14 falls at the approximate midpoint of the rails 60. Therefore, when viewed by a "normal" eye, the target 51 will appear perfectly forcussed when it is at the focal length of the lens 14 the lenses 16 and 18 are adjusted to have a net power of zero diopters.

A far sightedness condition would be indicated by the target being at its maximum clarity at a distance greater than the focal length of the lens 14. Similarly near sightedness is indicated by maximum target clarity at a distance less than the focal length. Suitable readout devices (not shown) to detect carriage position are therefore capable of providing a direct indication of the quantitative spherical correction necessary to maximize visual acuity. The carriage drive mechanism including motor 66 and arm 62 are arranged so that the carriage movement is relatively faster at its closest approach to the lens 14 and is relatively slower at its closest approach to the diffuser 70. In this manner the rate of change of focus presented to the viewer is substantially constant through the entire range of spherical diopter corrections. Thus, the carriage and carriage drive design results in a substantially constant change in diopter power per unit time so that a nearly linear read-out of the correction power may be obtained. In exemplary embodiment a range of from −8 to +7 diopters is provided.

During testing in a continuous movement mode, the strobe 74 is operated at approximately 16 flases per second thereby presenting numerous separate distinct images to the brain with relatively small diopter change for each image. The resolution of the system is to at least one quarter of a diopter.

While the system hs been described in conjunction with its use in association with an automatic vision examination system based on brain wave analysis it is to be understood that manual controls for all of the target and lens movements described herein may be provided so that the user can move the target to the position of maximum clarity and similarly can rotate the lenses in a manner comparable to that described hereinafter to manually obtain the necessary corrections.

After a determination of the spherical correction that produces maximum visual acuity, the device is operated in the cylindrical correction mode to determine the necessity for, and quantitative amount of, the astigmatic correction. The lenses 16 and 18 have substantial cylindrical power and are of substantially the same magnitude. The concave cylindrical lens 18 has slightly greater negative power than the positive power of the convex cylindrical lens 16. Therefore the lenses produce a net power of zero when the lens 18 is slightly out of contact with the lens 16. This avoids lens damage and a vacuum separation problem which would result if the lenses were of precisely the same power and had to be brought into contact to produce a net zero power. The cylindrical axis of the lenses is parallel, and therefore as the lens 18 is translated away from the lens 16 under the influence of drive nut 40, through the flexure mechanism 38, and increasing negative cylindrical power is obtained. In the exemplary embodiment a maximum of −3 diopters cylindrical correction is obtainable.

In the automatic mode the translation mechanism may be driven continuously from zero to −3 diopters and a simultaneous continuous rotation of the carrier 22 effected. The continuous rotation of the carrier 22 results in a complete range of cylindrical axis with each 180° of rotation. The effect of the flashing strobe 74 is such that the patient is exposed to a complete range of astigmatic corrections from zero to −3 diopters and at all axis orientations. The resolution of the system is to at least 10° in axis orientation and one quarter diopter of negative cylindrical power.

Having described my invention, I now claim:

1. An optical system for use in testing human vision as an aid in the prescription of corrective lenses and other vision examination, wherein the improvement comprises:
   a frame,
   lens means mounted on said frame for producing a spherical power of a nominal fixed focal length and a variable cylindrical power,
   said lens means comprising a first spherical lens fixedly mounted on said frame defining an optical axis, and first and second cylindrical lenses having substantial cylindrical power of substantially equal and opposite magnitude,
   said first and second cylindrical lenses being mounted on said frame for translation relative to one another along said optical axis and being rotatable about said optical axis,
   the cylindrical axes of said first and second cylindrical lenses being maintained parallel,
   a target,
   said target and said lens means being mounted on said frame for relative movement along said optical axis between points substantially less and substantially more than the nominal focal length of said lens means,
   and an eye piece mounted on said frame in position for viewing said target through said lens means.

2. An optical system for use in testing human vision as an aid in the prescription of corrective lenses and other vision examination as claimed in claim 1, wherein:
   said first and second lenses are arranged with concave and convex surfaces in opposition.

3. An optical system for use in testing human vision as an aid in the prescription of corrective lenses and other vision examination as claimed in claim 2, wherein:
   the relative translation of said first and second cylindrical lenses toward one another is limited to prevent actual contact between said concave and convex surfaces.

4. An optical system for use in testing human vision as an aid in the prescription of corrective lenses and other vision examination as claimed in claim 3, wherein:
   powers of said first and second cylindrical lenses differ by an amount sufficient to produce a combined power of zero when said lenses are translated to their closest approach.

5. An optical system for use in testing human vision as an aid in the prescription of corrective lenses and other vision examination as claimed in claim 1, wherein:
   said target is mounted on a carriage,
   said carriage is guided on rails,
   said rails are parallel to said optical axis.

6. An optical system for use in testing human vision as an aid in the prescription of corrective lenses and other vision examination as claimed in claim 5, wherein:
   said lens means comprises a rotatable cage fixed in translation along said optical axis between said viewing objective and said target,
   said rotatable cage mounts a lens having substantial cylindrical power,
   a lens transport carried in said cage for relative translation and mounting a lens having substantial cylindrical power,
   said lens transport being keyed for rotation with said cage.

* * * * *